United States Patent
Mickelson et al.

(10) Patent No.: US 6,229,901 B1
(45) Date of Patent: May 8, 2001

(54) AUDITORY FEEDBACK DEVICE

(76) Inventors: Nils Peter Mickelson, R.R. #3 Box 86F, Gorham, ME (US) 04038; Raymond C. Miller, 57 Massachusetts Ave., Portland, ME (US) 04102

( * ) Notice: Subject to any disclaimer, the term of this patent is extended or adjusted under 35 U.S.C. 154(b) by 0 days.

(21) Appl. No.: 09/035,585

(22) Filed: Mar. 5, 1998

(51) Int. Cl.[7] .................................................. H04R 25/00
(52) U.S. Cl. .......................... 381/371; 181/128; 181/129; 181/136
(58) Field of Search ........................... 381/371; 181/126, 181/127, 128, 129, 133, 136

(56) References Cited

U.S. PATENT DOCUMENTS

| 3,618,698 | 11/1971 | McCabe | 181/25 |
| 3,895,188 | * 7/1975 | Ingraham | 381/160 |
| 3,938,616 | 2/1976 | Brownfield | 181/136 |
| 4,321,853 | 3/1982 | Tumblin | 84/470 R |
| 4,732,072 | 3/1988 | Garlock | 84/470 R |
| 4,771,859 | * 9/1988 | Breland | 181/136 |
| 4,997,056 | 3/1991 | Riley | 181/136 |
| 5,061,186 | 10/1991 | Jost | 434/185 |
| 5,345,512 | 9/1994 | Lee | 381/183 |
| 5,557,056 | 9/1996 | Hong | 84/610 |
| 5,565,639 | 10/1996 | Bae | 84/477 R |
| 5,881,150 | * 3/1999 | Persson | 379/433 |

OTHER PUBLICATIONS

Bruce Medical Supply product information bulletin, 1997 ADDvox III Speech Enhancer.
Voice Imaging, Inc. product information bulletin, 1992 The Voice Imaging Loop.
DLM–SRA Catalog, 1987: p. 67 TOK–BACK speech mask.

* cited by examiner

Primary Examiner—Forester W. Isen
Assistant Examiner—Brian Tyrone Pendleton
(74) Attorney, Agent, or Firm—Nils Peter Mickelson

(57) ABSTRACT

An auditory feedback device is provided for singers or the hearing-impaired to better hear their own voice. The device uses sound guides with reflective surfaces shaped to reflect sounds from the user's mouth to the user's ear.

14 Claims, 4 Drawing Sheets

AUDITORY FEEDBACK DEVICE

CROSS-REFERENCE TO RELATED APPLICATIONS

Not applicable

STATEMENT REGARDING FEDERALLY SPONSORED RESEARCH OR DEVELOPMENT

Not applicable

BACKGROUND OF THE INVENTION

This invention relates to the field of apparatus for improving speech or singing by enhancing feedback from a user's mouth to the user's ear.

There are times when it's helpful to hear oneself better—for example when singing as part of a chorus or when one's hearing is impaired. We hear our own voice by a combination of vibrations conducted through flesh and bone directly to the inner ear and cochlea, and by back-scattering, refraction or distant reflection of sound waves emanating from our mouth. Hearing aids—and previously, ear trumpets—augment hearing generally, but with no intent to selectively provide personal feedback. However, when air-transmitted hearing is overwhelmed by ambient sound or impaired by sound absorption or reduced ear sensitivity, it is a great benefit to enhance feedback.

Prior art includes numerous inventions meant for hearing distant sounds more clearly. Examples include U.S. Pat. Nos. 3,618,698 to McCabe (1971), 3,938,616 to Brownfield (1976), 4,997,056 to Riley (1991), and 5,345,512 to Lee (1994). In all cases, these direct their efforts to hearing remote sounds, specifically from in front of the user. To varying degrees, these also incorporate adjustment, mounting or alignment features to fit individual heads and to direct sound from a distance into a user's ears.

Electronics has engendered elaborate and expensive systems for personal feedback, involving (at the least) a microphone, amplifier, headphones and associated cabling. With these, and a source of power, the function of feedback may be fulfilled. One such system is the so-called Voice Imaging system by Voice Imaging, Incorporated; another is the ADDVOX III by Bruce Medical Supply. Others are disclosed in U.S. Pat. Nos. 4,732,072 (1988) to Garlock, 4,321,853 (1982) to Tumblin, 5,557,056 to Hong (1996), 5,565,639 to Bae (1996), and 5,061,186 to Jost (1991), roughly in order of their increasing complexity.

All of these suffer from intricacy, high cost, and the need for a source of power.

A variety of improvisations, such as cupping a hand to the cheek, cutting a crude shape from a milk container or making a sound pipe from pieces of commercially available tubing, has been contrived to fill the need for personal feedback. The only prior art directed to the purpose of personal feedback is a product named Tok-Back—a single piece kidney-shaped molding of thin, soft elastomeric material formed to cover and enclose the user's ears, mouth, cheeks and chin to trap sound pressure emanating from the mouth. As such, it is cumbersome, awkward, unsanitary and obtrusive to use, requires periodic repositioning on the face and suffers from extreme internal resonances.

BRIEF SUMMARY OF THE INVENTION

To provide simply and effectively a means for hearing oneself better, our feedback device uses a reflective surface shaped to focus and direct one's own voice into one's own ear canal. This reflective surface may be used singly, or in a right-left pairing for symmetry, and may be provided with a means for holding or a means for mounting to the user's head.

Figure 1:
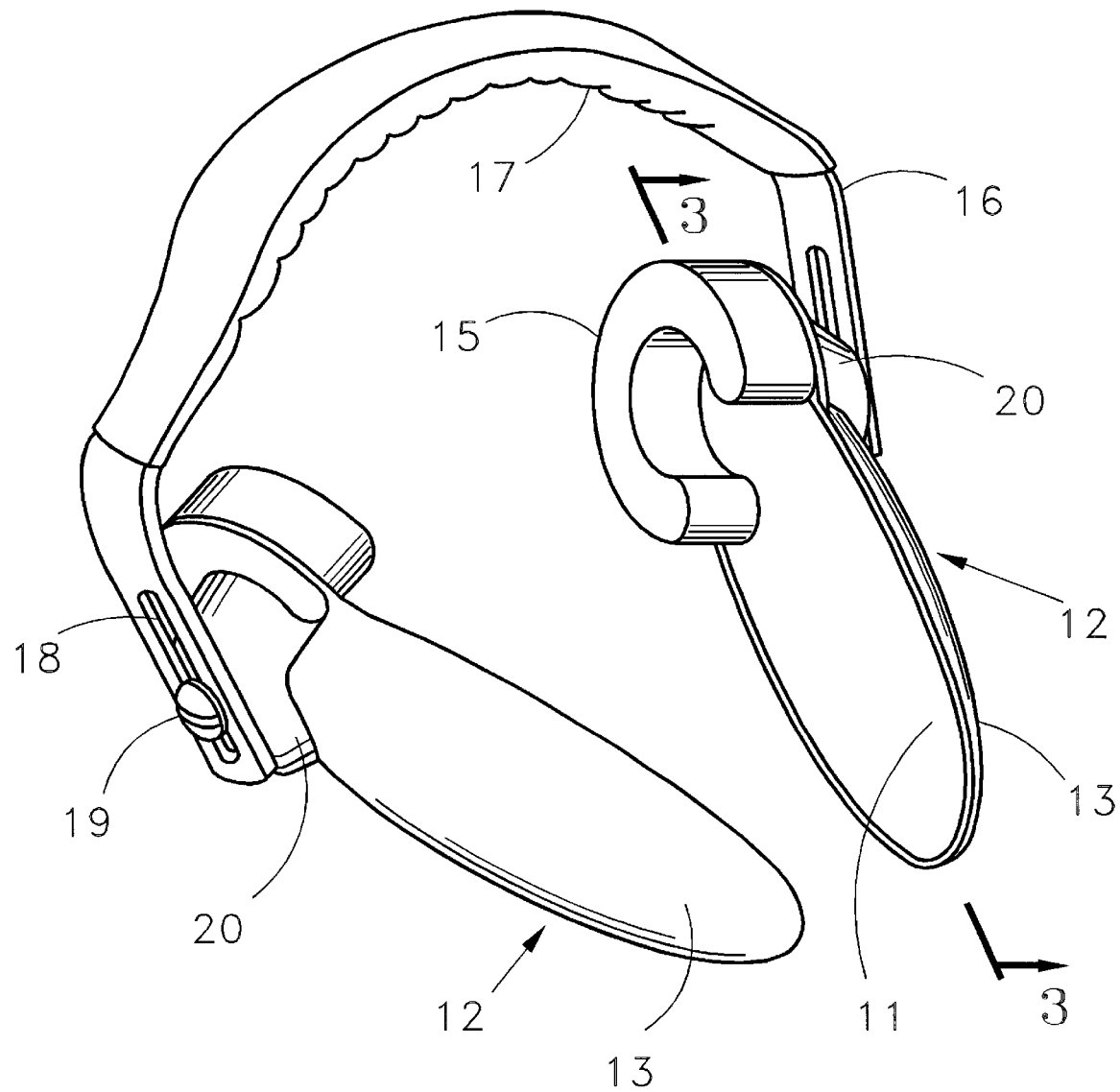
FIG. 1 provides an overall view of the preferred embodiment of our auditory feedback device.

REFERENCE NUMERALS USED IN DRAWINGS 11 reflective surface 19 fastener
12 sound guide 20 hub
13 outer surface 21 hole
14 sound guide molding 22 grommet
15 ear pad 23 surface
16 head band M first focal point
17 head band pad E second focal point
18 slot

DETAILED DESCRIPTION OF THE INVENTION

Figure 2:
FIG. 2 illustrates the device in use.

FIG. 1 depicts an overall view of the preferred embodiment of our auditory feedback device. Two sound guides 12 are each attached by a fastener 19 to a head band 16. From FIG. 2 it may be seen that this embodiment is worn on the user's head such that sounds emanating from the user's mouth are reflected into each of the user's ears. Details of the construction and principle of operation are set forth below.

Figure 3A:
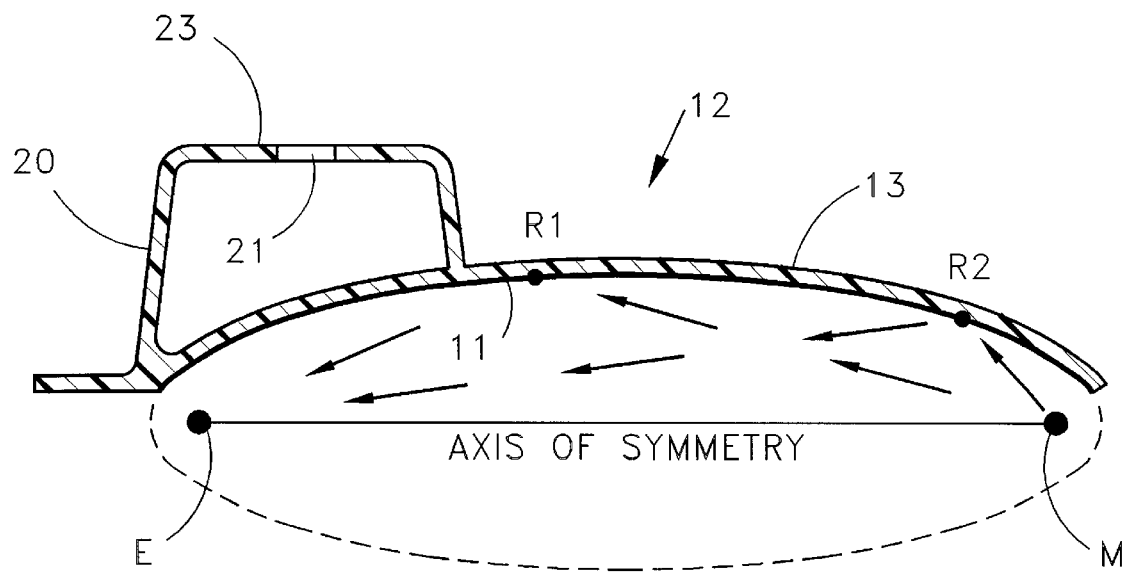
FIGS. 3a and 3b show the principle of operation of two alternative shapes for a reflective surface as taken by section lines 3—3 in FIG. 1.

In FIG. 1, the basis of our device is seen to be an acoustically reflective surface 11 formed as part of a sound guide 12 and shaped to focus one's own voice into one's own ear canal. In the preferred embodiment, this surface is an ellipsoidal surface, best seen by cross-section 3—3 as shown in FIG. 3a.

An ellipsoidal surface is characterized by two focal points which define its axis of symmetry and by a shape factor known as eccentricity. All paths from one focal point to the other focal point which reflect off reflective surface 11 have equal length. By proper orientation of axis and choice of eccentricity, a first focal point of reflective surface 11, shown in FIG. 3 at M, may be centered on the user's mouth while the second focal point, shown at E, may be centered on the opening of the user's ear. Thus, sounds emanating from the mouth at M are efficiently reflected along equal-length paths to the ear at E with no phase distortion caused by unequal travel times.

While reflective surface 11 is sufficient in itself to provide feedback and meet the function of our device, it is generally preferred to equip one end of sound guide 12 with an ear pad 15 to improve comfort and to help locate it spatially in relation to the ear during use. Ear pad 15 should preferably be of a compliant acoustically transparent material, such as an open cell, or reticulated, polymeric foam. Such a material distributes the pressure of holding sound guide 12 against the ear and dampens resonance, while not appreciably attenuating surrounding sounds.

Though ear pad 15 could alternatively be made from acoustically opaque material, it would suffer the disadvantage of isolating the user from the environment and of acoustically closing one end of sound guide 12, thus creating resonance effects. This isolating would be only a minor problem when using our device in a solo context, or simply to augment feedback with lesser concern for sound quality, as perhaps when commencing to train a person with hearing or speech impairment.

Ear pad 15 may be fastened to sound guide 12 by any conventional method such as a pressure sensitive adhesive or removable hook-and-loop tape.

While our feedback device may well be used by holding a single sound guide 12 against one ear, using two sound guides provides more feedback and a more symmetric sound. Indeed, it's often helpful to use our device while leaving the hands free, for example to hold text or music sheets. Thus, the preferred embodiment includes a mounting means such as an adjustable head band 16, typical of headphones, hearing protectors, and the like. For improved comfort, head band 16 may be equipped with a head band pad 17 which bears gently against the head during use. Pad 17 may be affixed to head band 16 by any method such as adhesive, insert molding in place, or slipping it over head band 16.

Figure 4:
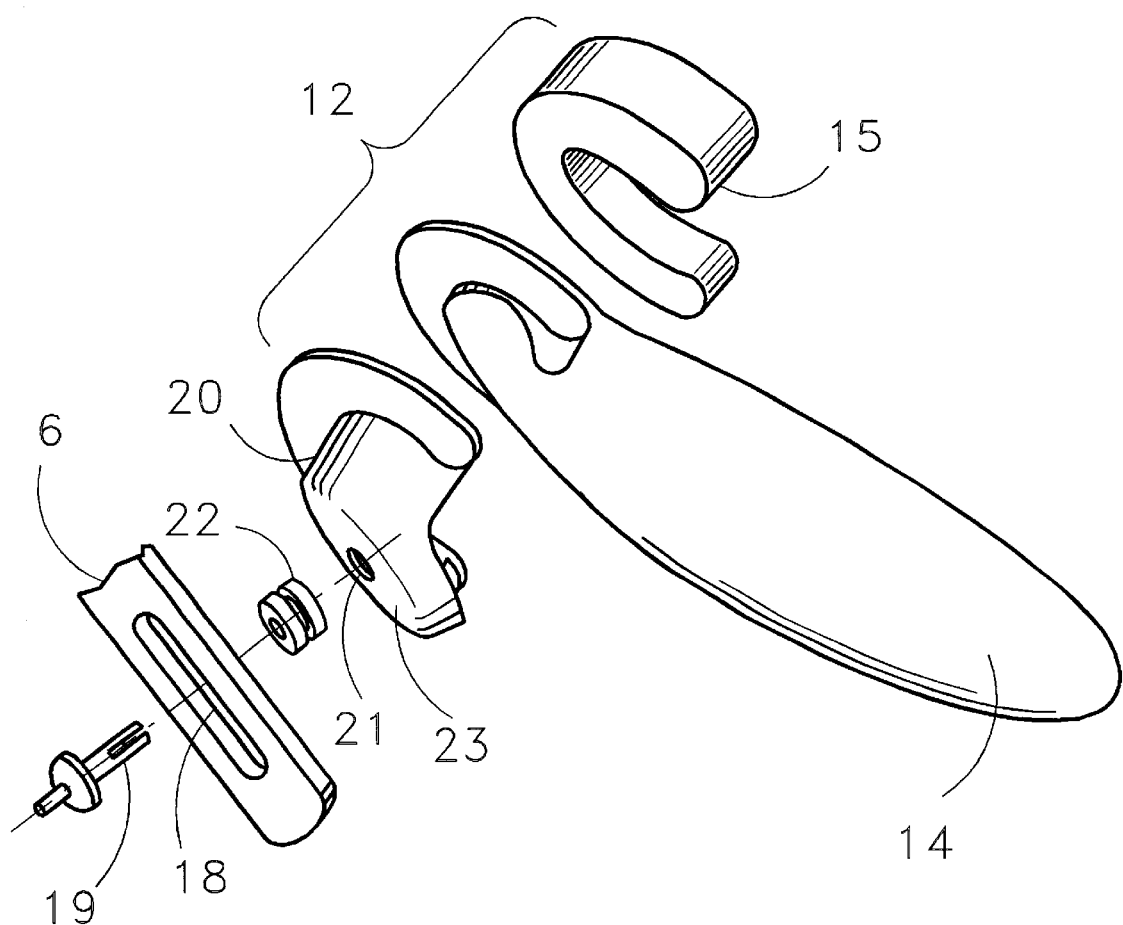
FIG. 4 is an exploded view of a portion of the preferred embodiment showing assembly details.

Attaching sound guides 12 to any mounting such as a head band 16 should be done with an eye to adjustment for different users. Such adjustment should include a method to adjust for the size of the user's head, as provided by slots 18, and a method for aligning sound guide 12 with the user's mouth, as provided by use of an axial fastener 19, such as a screw (shown in FIG. 1) or a rivet (as shown in FIG. 4). Alternatively, the alignment method may also be used to more or less disable a sound guide 12 by rotating it out of position, should feedback be excessive under certain conditions.

Since inner reflective surface 11 itself serves the purpose of our device, outer surface 13 of sound guide 12 may take any form, and the sound guide's materials of construction may comprise any acoustically reflective substance. For aesthetic and other reasons, the preferred embodiment uses an outer surface 13 closely paralleling much of inner reflective surface 11, forming thereby a uniformly thin and light weight shell to minimize weight and inertia, and is made from a colorless, optically clear material such as an acrylic plastic to maximize field of vision and to minimize obtrusiveness of the device as seen by others.

At its end nearest the user's ear, outer surface 13 in the preferred embodiment departs from inner reflective surface 11 to generally form a hub 20 suitable for engaging fastener 19. Here the space between the inner and outer surfaces deepens and may be substantially filled, as with a solid or foam core material, or substantially empty, as would be formed between two thin divergent shells.

In the preferred embodiment, best understood in FIG. 4, hub 20 is molded as a separate thin-walled part by thermoforming or a like process, and affixed to a similarly-made sound guide molding 14 at the periphery of ear pad 15 by any common process such as adhesive bonding, welding or staking. Hub 20 may be provided with a hole 21 through which fastener 19 may extend, and this hole may be equipped with a grommet 22 made of a resilient material such as an elastomer. Partial compression of grommet 22 by fastener 19 provides friction to the adjustment laterally along slot 18 and rotationally around fastener 19.

Use of a resilient grommet 22 in hole 21 also provides a degree of compliance or flexibility at the fastening point, which may be desirable for comfort on a variety of users. For additional flexibility, surface 23 of hub 20 surrounding hole 21 may be made substantially thin, flat and flexible to enhance flection.

In lieu of hub 20, and by apppropriately shaping outer surface 13, it's clear that a handle or the like could be formed on sound guide 12, for when the device is hand held or used singly, thus obviating any headband and fastener components.

An ellipsoidal surface serves to direct sound effectively from the mouth to the ear, as shown in FIG. 3a. Sounds emanating from the mouth in the vicinity of a first focal point M are reflected off the entirety of reflective surface 11 via paths represented by the arrows reflecting at points R1 and R2 and arriving at second focal point E in the vicinity of the user's ear canal. Because each path has equal length, sounds arrive exactly in phase and with a minimum of distortion.

But there may occur the need for elongating or otherwise modifying the shape of the sound guide, for example to accommodate unusual heads or for aesthetic reasons. In such case, as shown in FIG. 3b, two co-aligned paraboloidal surfaces may be used in lieu of a single ellipsoidal surface.

Figure 3B:
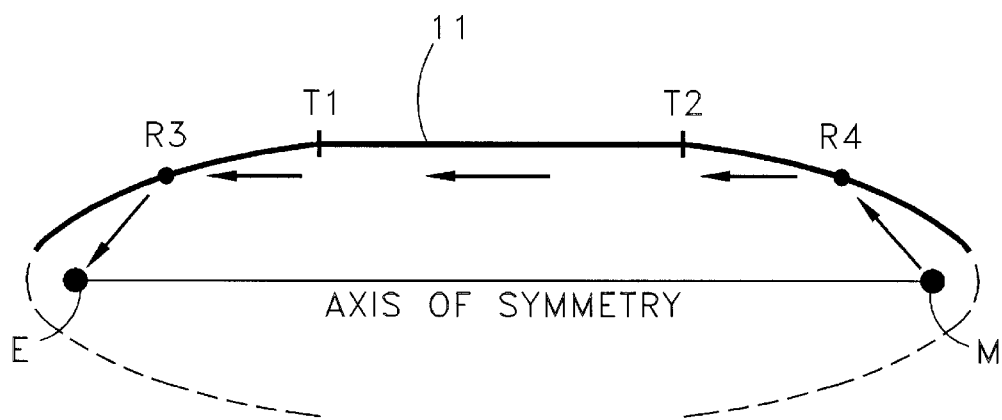

A practical way to provide such an arrangement is to form both paraboloidal surfaces as part of one component, connected by a co-aligned cylindrical section as shown in FIG. 3b between transition points T1 and T2. This alternative form of reflective surface 11 causes two reflections to occur for each path, as represented by the arrows from first focal point M to points R4 and R5 and on to second focal point E.

From the above, one understands that our invention fills a need not earlier satisfied, and so effectively that scores of people have consistently remarked either "Wow!" or "Oh, wow!" when they first try it. It should be clear that our invention lies in the reflective surface, and that how this surface is held in place is relatively less important. Simple advantages mentioned by users include open access to the mouth in case one wishes to sip a drink or a throat lozenge, the ability to sneeze without sanitary concerns and the openness to easy breathing without the odor of polymeric materials close to the nose.

Though the above description is necessarily specific, many alternatives to materials and structures may be used to accomplish the same results, such as sheet metal reflective surfaces or any of the many adjustment means typical of the wide variety of head bands commonly used in headphones, hearing protectors, ear muffs and the like. The scope of our invention should be determined by the appended claims rather than by the specific embodiments recited above.

We claim:

1. An auditory feedback device comprising an elongated sound guide with an acoustically reflective surface, said acoustically reflective surface shaped about an axis of symmetry and extending from a user's ear to said user's mouth to reflect and focus sound emanating from said user's mouth via direct acoustic paths of equal length with no phase distortion caused by unequal travel times into said user's ear, whereby said user may hear his or her own voice more clearly.

2. The device of claim 1 wherein said acoustically reflective surface is an ellipsoid.

3. The device of claim 1 wherein said acoustically reflective surface comprises a pair of co-aligned paraboloidal surfaces.

4. The device of claim 3 wherein said co-aligned paraboloidal surfaces are joined by a co-aligned cylindrical section.

5. The device of claim 1 wherein said elongated sound guide is optically clear.

6. The device of claim 1 further comprising, on said elongated sound guide, a pad for bearing against said user's ear.

7. The device of claim 6 wherein said pad is comprised of open cell foam, whereby ambient sounds may be freely heard.

8. The device of claim 1 further comprising mounting means for mounting said elongated sound guide on said user to allow hands-free operation.

9. The device of claim 8 wherein said mounting means is a head band.

10. The device of claim 1 further comprising a head band and an adjustable fastening means, said elongated sound guide connected to said head band by said adjustable fastening means.

11. The device of claim 10 wherein said adjustable fastening means comprises an axial fastener, a grommet, and a flexible surface surrounding a hole, said grommet installed in said hole and around said fastener, whereby flexure of said surface and compression of said grommet provide compliance and friction to said adjustable fastening means.

12. A method of providing personal auditory feedback comprising aligning with a user's ear and mouth an elongated acoustically reflective surface shaped about an axis of symmetry and extending from said user's ear to said user's mouth and of a shape predetermined to reflect and focus sound emanating from said user's mouth via direct acoustic paths of equal length with no phase distortion caused by unequal travel times into said user's ear.

13. The method of claim 12 in which said elongated acoustically reflective surface is an ellipsoid.

14. The method of claim 12 in which said elongated acoustically reflective surface comprises a pair of co-aligned paraboloidal surfaces joined by a co-aligned cylindrical section.

* * * * *